United States Patent [19]
Grinberg

[11] Patent Number: 5,755,731
[45] Date of Patent: May 26, 1998

[54] CURVED SURGICAL INSTRUMENT WITH SEGMENTED INNER MEMBER

[75] Inventor: Alexander Grinberg, Newton, Mass.

[73] Assignee: Smith & Nephew Dyonics, Inc., Andover, Mass.

[21] Appl. No.: 575,173

[22] Filed: Dec. 19, 1995

Related U.S. Application Data

[63] Continuation of Ser. No. 425,719, Apr. 20, 1995, abandoned, which is a continuation of Ser. No. 228,083, Apr. 15, 1994, abandoned.

[51] Int. Cl.$^6$ .................................................. A61B 17/32
[52] U.S. Cl. ............................. 606/170; 606/180; 604/22
[58] Field of Search ........................ 606/170, 171, 606/180, 181; 604/22; 128/4–6, 750–755

[56] References Cited

U.S. PATENT DOCUMENTS

| | | |
|---|---|---|
| 1,677,337 | 7/1928 | Grove . |
| 3,618,611 | 11/1971 | Urban . |
| 3,734,099 | 5/1973 | Bender et al. . |
| 3,837,345 | 9/1974 | Matar . |
| 3,937,222 | 2/1976 | Banko . |
| 3,945,375 | 3/1976 | Banko . |
| 4,071,029 | 1/1978 | Richmond et al. . |
| 4,108,211 | 8/1978 | Tanaka . |
| 4,167,943 | 9/1979 | Banko . |
| 4,167,944 | 9/1979 | Banko . |
| 4,200,106 | 4/1980 | Douvas et al. . |
| 4,203,444 | 5/1980 | Bonnell et al. . |
| 4,274,414 | 6/1981 | Johnson et al. . |
| 4,320,761 | 3/1982 | Haddad . |
| 4,328,839 | 5/1982 | Lyons et al. . |
| 4,347,837 | 9/1982 | Hosono .................... 128/6 |
| 4,362,520 | 12/1982 | Perry . |
| 4,432,349 | 2/1984 | Oshiro . |
| 4,436,091 | 3/1984 | Banko . |
| 4,497,320 | 2/1985 | Nicholson et al. . |
| 4,512,344 | 4/1985 | Barber . |
| 4,517,977 | 5/1985 | Frost . |
| 4,541,423 | 9/1985 | Barber . |
| 4,589,414 | 5/1986 | Yoshida et al. . |
| 4,598,710 | 7/1986 | Kleinberg et al. . |
| 4,600,037 | 7/1986 | Hatten . |
| 4,603,694 | 8/1986 | Wheeler . |
| 4,646,738 | 3/1987 | Trott .......................... 606/180 |
| 4,649,919 | 3/1987 | Thimsen et al. . |
| 4,660,267 | 4/1987 | Wheeler . |
| 4,662,371 | 5/1987 | Whipple et al. . |
| 4,672,965 | 6/1987 | Baum . |
| 4,706,659 | 11/1987 | Matthews et al. . |
| 4,723,545 | 2/1988 | Nixon et al. . |
| 4,738,256 | 4/1988 | Freeman et al. . |
| 4,756,309 | 7/1988 | Sachse et al. . |
| 4,770,174 | 9/1988 | Luckman et al. . |
| 4,773,395 | 9/1988 | Suzuki et al. . |

(List continued on next page.)

FOREIGN PATENT DOCUMENTS

| | | |
|---|---|---|
| 0 445 918 A1 | 5/1991 | European Pat. Off. . |
| 0 481 760 A1 | 4/1992 | European Pat. Off. . |
| 0 612 496 A1 | 1/1994 | European Pat. Off. . |
| 3828478A1 | 5/1989 | Germany . |
| 906-301-A | 12/1989 | Germany . |
| 4302912 A1 | 8/1994 | Germany . |
| 153147 | 9/1919 | United Kingdom . |
| 1235321 | 6/1971 | United Kingdom . |
| 2222953 | 3/1990 | United Kingdom . |
| WO92/08416 | 5/1992 | WIPO . |
| 9215255 | 9/1992 | WIPO .................... 604/22 |
| WO92/15255 | 9/1992 | WIPO . |
| WO93/04634 | 3/1993 | WIPO . |
| WO93/13713 | 7/1993 | WIPO . |

*Primary Examiner*—William Lewis
*Attorney, Agent, or Firm*—Fish & Richardson P.C.

[57] ABSTRACT

A surgical instrument includes an inner member having a plurality of interengaging segments that are disposed within a bend region of an elongated outer member. The interengaging segments transmit force applied to a proximal region of the inner member through the bend region to cause a cutting implement at a distal region of the inner member to move and cut tissue admitted through an opening at the distal end of the outer member.

15 Claims, 2 Drawing Sheets

U.S. PATENT DOCUMENTS

| | | |
|---|---|---|
| 4,790,312 | 12/1988 | Capuano, Sr. et al. . |
| 4,811,734 | 3/1989 | McGurk-Burleson et al. . |
| 4,834,069 | 5/1989 | Umeda . |
| 4,834,729 | 5/1989 | Sjostrom . |
| 4,844,064 | 7/1989 | Thimsen et al. . |
| 4,850,354 | 7/1989 | McGurk-Burleson et al. . |
| 4,867,155 | 9/1989 | Isaacson . |
| 4,923,441 | 5/1990 | Shuler . |
| 4,983,179 | 1/1991 | Sjostrom . |
| 5,047,008 | 9/1991 | de Juan, Jr. et al. . |
| 5,100,426 | 3/1992 | Nixon . |
| 5,112,299 | 5/1992 | Pascaloff . |
| 5,114,399 | 5/1992 | Kovalcheck . |
| 5,143,475 | 9/1992 | Chickama . |
| 5,152,744 | 10/1992 | Krause et al. ............... 604/22 |
| 5,176,126 | 1/1993 | Chikama . |
| 5,178,129 | 1/1993 | Chikama et al. . |
| 5,179,934 | 1/1993 | Nagayoshi et al. . |
| 5,179,935 | 1/1993 | Miyagi . |
| 5,197,767 | 3/1993 | Kimura et al. . |
| 5,285,795 | 2/1994 | Ryan et al. ............... 606/171 |
| 5,320,635 | 6/1994 | Smith . |

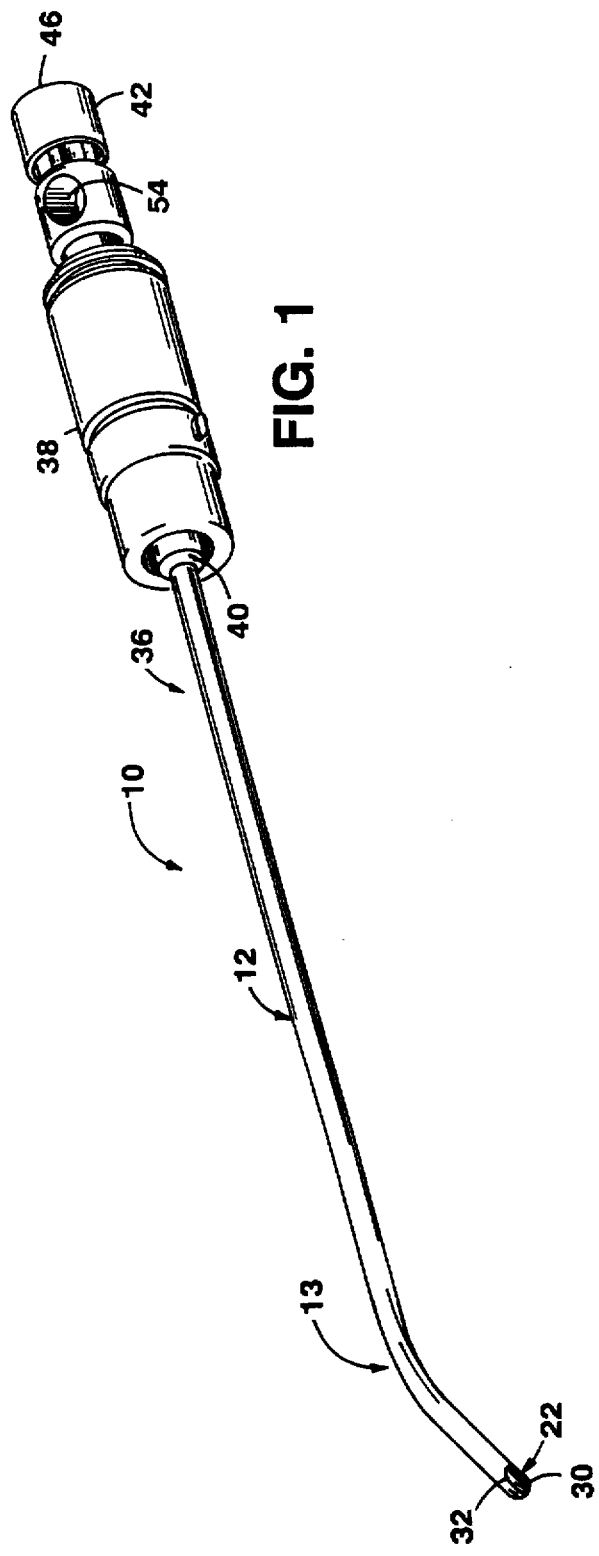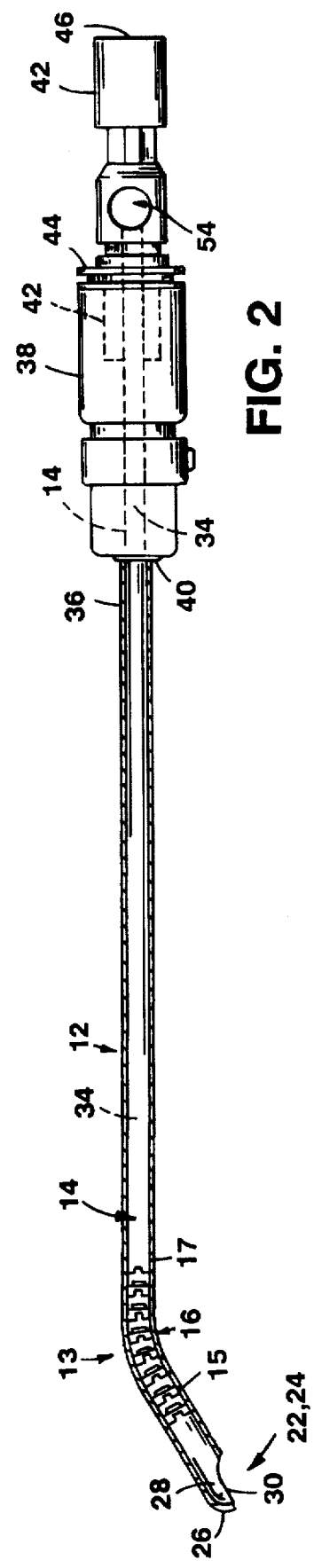

CURVED SURGICAL INSTRUMENT WITH SEGMENTED INNER MEMBER

This is a continuation of application Ser. No. 08/425,719, filed Apr. 20, 1995, now abandoned, which is a continuation of application Ser. No. 08/228,083, filed Apr. 15, 1994, which is abandoned.

BACKGROUND OF THE INVENTION

This invention relates to arthroscopic surgical instruments.

Arthroscopic surgical instruments typically include a rigid outer tube within which a rigid inner tube is rotated, for example, by a motor. A cutting implement, such as a blade or abrading burr, is disposed on the distal end of the inner tube. Tissue or bone is exposed to the cutting implement through an opening in the distal end of the outer tube, and tissue or bone fragments cut by the rotating blade or burr are drawn through the interior of the inner tube along with irrigating fluid by the use of suction applied at the proximal end of the instrument.

Typical arthroscopic surgical instruments are linear, that is, straight between their proximal and distal ends. It is sometimes useful for such instruments to be curved to facilitate positioning the cutting implement against tissue to be cut without requiring that the instrument be removed from the body and reinserted through an additional puncture. In curved instruments, the region of the inner tube that lies within the curved section of the outer tube is flexible to enable the inner tube to accept the curvature imposed by the outer tube while transmitting torsion from the motor to the cutting implement.

SUMMARY OF THE INVENTION

In one general aspect of this invention, the inner member of a surgical instrument includes a plurality of interengaging segments disposed within a bend region of an elongated outer member of the instrument; the interengaging segments transmit force applied to a proximal region of the inner member through the bend region to cause a distally-mounted cutting implement to move and cut tissue admitted through an opening at the distal end of the outer member.

Preferred embodiments include the following features.

Each of the interengaging segments includes at least one tab that extends axially from one end of the segment, and at least one slot disposed in an opposite end of the segment. The tab of each segment is received by the slot of an adjacent segment. The tab and slot of each segment are offset from each other by 90° about the longitudinal axis of the segment. Thus, adjacent segments are rotated with respect to each other by 90° within the bend region.

The length of each segment is sufficiently small to enable the segment to freely move within the bend region. A sufficient number of interengaging segments are provided so as to occupy at least the entire length of the bend region. The cutting implement (e.g., a blade) and the proximal region of the inner member also include at least one axially extending tab (or, alternatively, at least one slot) for engaging the proximal-most and distal-most segments.

The lengths of the tabs exceed the depths of the slots, and the widths of the tabs are less than the widths of the slots. The tabs have rounded end surfaces for providing smooth rolling surfaces between the engaging tabs and slots of adjoining segments. These features provide a loose-fitting connection between the interengaging segments in the bend region, which reduces the level of fatigue stresses that can develop between the segments during operation. Because the inner member may be rotated over a large range of speeds and applied torque (e.g., by a motor that drives the proximal end of the inner member), it is important that fatigue stresses be as small as possible to reduce the risk of breakage. The tabs and slots also have rounded corners (or fillets) to avoid shedding of material from the segments during operation.

The inner member and the plurality of interengaging segments are hollow and define a suction passage for transporting tissue cut by the cutting implement. A flexible sheath, formed of, e.g., heat shrink tubing, surrounds the interengaging segments and adjacent portions of the inner member and the cutting implement. The sheath seals the suction passage so that the fragments are efficiently transported through the passage (in response to suction applied to the proximal end of the inner member) while the instrument remains in situ for further cutting.

The interengaging segments of the inner member conform to the curvature imposed by the bend region of the outer member while maintaining a high degree of torsional and axial stiffness. As a result, the segments efficiently transmit torque (or other forces) past the bend region to the cutting implement for high efficiency cutting. The configuration of the interengaging segments provides a rugged and reliable surgical instrument with increased life that is relatively easy to manufacture and assemble. Moreover, the cost of manufacture is generally less than inner members having one-piece flexible designs.

Additionally, whether the outer member is straight or curved, the interengaging segments accommodate themselves to axial deviations in the outer member. As a result, deviations (actually minor bends in the outer member that can occur during the rigors of surgery) which may otherwise cause the inner member to bind during rotation or the cutting implement to periodically pull away from the edges of the outer member openings as the inner member rotates, have little or no effect on the cutting efficiency of the instrument.

Other features of the invention will be apparent from the following description and from the claims.

BRIEF DESCRIPTION OF THE DRAWING

FIG. 1 shows a curved arthroscopic surgical instrument.

FIG. 2 shows the instrument of FIG. 1 with the outer tube in cross-section to reveal the inner tube.

DECSRIPTION OF A PREFERRED EMBODIMENT

Figure 3:
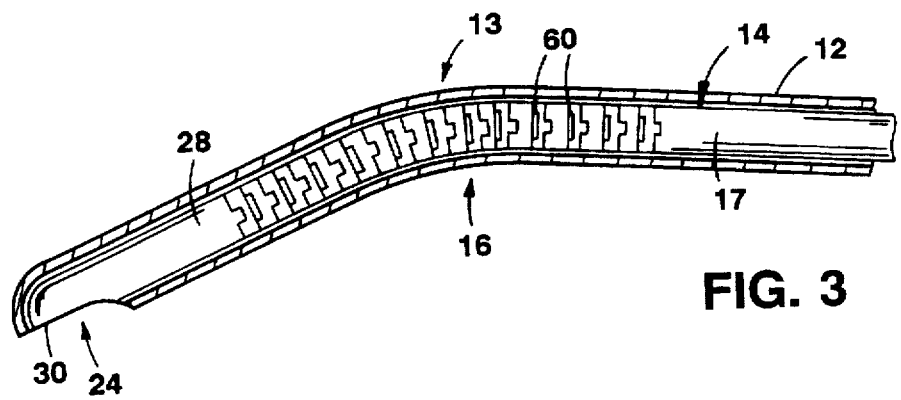
FIG. 3 is an enlarged view of a portion of the instrument of FIG. 2, showing a plurality of interengaging segments that render the inner tube flexible within the bend region of the outer tube.

Referring to FIGS. 1 and 2, surgical instrument 10 suitable for arthroscopic surgery (e.g., closed, arthroscopic surgery on a knee) includes a rigid, stationery hollow outer tube 12 within which is disposed a rotating hollow inner tube 14. A bend region 13 of outer tube 12 enables instrument 10 to operate on surgical areas that are difficult to reach with a straight instrument. The proximal region 17 and the distal region 28 of inner tube 14 are rigid and are coupled together by a flexible region 16 that accepts the curvature imposed by bend region 13 while transmitting torsion (or other forces) applied to the proximal end of inner tube 14 to a cutting implement 30 on distal region 28.

Referring to FIGS. 3, 4, and 5a-5c, flexible region 16 includes a set of hollow, cylindrically shaped interengaging segments 60 that link cutting implement 30 to proximal region 17 of inner tube 14. Segments 60 occupy at least all of bend region 13 and may extend both proximally and distally within adjacent straight sections of outer tube 12, as desired. The interengaging nature of segments 60 provides sufficient flexibility to transmit forces through bend region 13 to rotate cutting implement 30 and cause to cut tissue that extends through opening 22 in outer tube 12. In addition, interengaging segments 60 provide a high degree of axial stiffness to maintain cutting implement 30 aligned with opening 22.

Figure 5A:
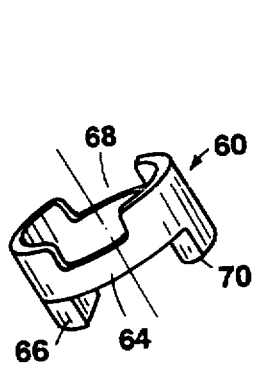
FIGS. 5a-5c are three views of one of the interengaging segments.
Figure 5B:
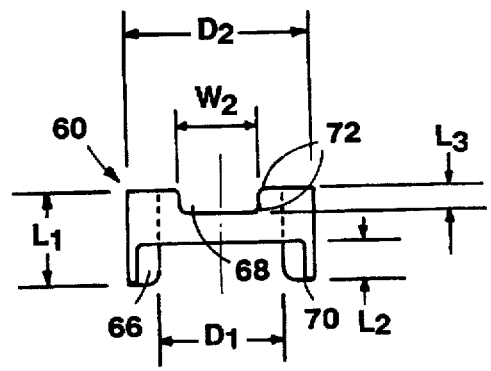
Figure 5C:
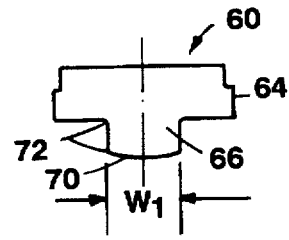

Each segment 60 (also called a cardan joint) includes a ring 64. A pair of tabs 66 extend axially from one end of ring 64 in diametrically opposing fashion with a pair of slots 68 formed on the opposite end of ring 64 (FIG. 5a). Tabs 66 of each segment 60 are received by slots 68 of the adjacent segment 60. In each segment, tabs 66 are angularly offset from slots 68 by 90° about the longitudinal axis of the segment. This allows the axial dimension of segments 60 to be relatively small so that segments 60 can accept large degrees of curvature. As a result of the orientation of tabs 66 and slots 68, adjacent segments 60 are rotated with respect to each other by 90° about the longitudinal axis of segments 60. The length (L1) of each segment 60 should be sufficiently small to enable segment 60 to freely rotate within bend region 13 during operation.

Figure 4:
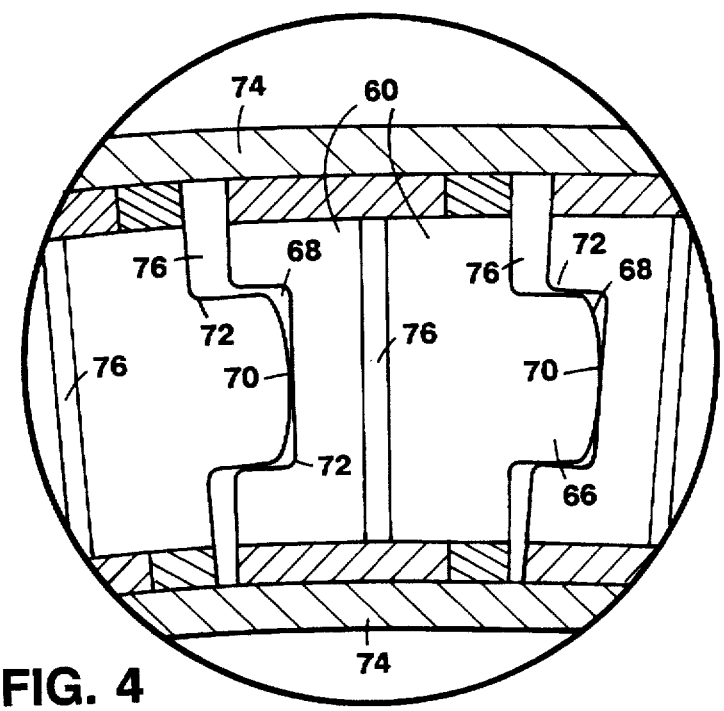
FIG. 4 shows a further enlargement, in cross-section, of some of the interengaging segments of FIG. 3.

Tabs 66 have rounded end surfaces 70 for providing smooth rolling surfaces between tabs 66 and slots 68 of adjoining segments 60. Tabs 66 and slots 68 have rounded corners 72 to reduce the risk of shedding during operation. The length L2 and width W1 of each tab 66 are longer and smaller than the depth L3 and width W2 of the slot 68 to be engaged. The geometry of tabs 66 and slots 68 provide loose fitting connections between adjacent pairs of interengaging segments 60 along the length of bend region 13 and, as shown most clearly in FIG. 4, provide spaces 76 between segments 60 for allowing tabs 66 to move freely within associated slots 68 during rotation of inner tube 14. Typical dimensions for an interengaging segment 60 used with bend region 13 having a radius of curvature of 1.06 inches as follows (see FIG. 5b):

| Length of segment (L1) | 90 mils |
| Inner diameter (D1) | 106 mils |
| Outer diameter (D2) | 134 mils |
| Length of tab (L2) | 29 mils |
| Width of tab (W1) | 55 mils |
| Depth of slot (L3) | 19 mils |
| Width of slot (W2) | 59 mils |
| Radius of tab end | 100 mils |
| Radius tab/slot corners | 5 mils |

Segments 60 are formed using injection molding or, alternatively, rings 64 of segments 60 may be molded or extruded with tabs 66 and slots 68 formed using a wire EDM (electron discharge machine) process.

The hollow interiors of proximal region 17 and distal region 28 of inner tube 14 and segments 60 define a suction passage 34 through which tissue cut by implement 30 is removed while instrument 10 remains in situ for further cutting. Openings 76 between adjacent segments 60 are sealed by a flexible sheath 74 that surrounds segments 60 and adjacent portions of proximal region 17 and distal region 28 of inner tube 14. Sheath 74 has a wall thickness of less than 0.001 inches and is made from a heat shrinkable polyester having a pre-shrunk inner diameter of 148 mils and a wall thickness of less than 1 mil. This material is available from Advanced Polymers Inc., Salem, NH. Sheath 74 is placed over segments 60 and the adjacent portions of proximal region 17 and distal region 28, and is then heated (for example, in a heat shrink tunnel) sufficiently to contract sheath 74 tightly around segments 60 and proximal and distal regions 17, 28.

Referring again to FIGS. 1 and 2, proximal end 36 of outer tube 12 and proximal region 17 of inner tube 14 are received by a base 38. Outer tube 12 is rigidly mounted to base 38 at a sealed joint 40, while inner tube 14 is secured to a drive shaft 42 that rotates within base 38. Suction passage 34 terminates in a vacuum source opening 54 in drive shaft 42. Drive shaft 42 is retained with base 38 by a pliable fitting 44.

The material used for tubes 12, 14 and segments 60 depends on, among other factors, the toughness of the tissue to be cut and whether instrument 10 is disposable or reusable. For a disposable instrument designed for general purpose arthroscopic surgery, tubes 12, 14 are fabricated from 304 stainless steel. Segments 60 are made from injection molded plastic. Base 38 and its components (e.g., drive shaft 42) are plastic, but metal may be used as an alternative (e.g., for reusable instruments).

The proximal end 46 of drive shaft 42 fits into a handpiece (not shown), which includes a motor for rotating drive shaft 42 and inner tube 14. One example of such a handpiece is described in U.S. Pat. No. 4,705,038, entitled "Surgical System for Powered Instruments", assigned to the present assignee, and incorporated herein by reference. Fitting 44 provides a fluid-tight seal when base 38 is inserted into the handpiece.

In operation with instrument 10 inserted into the handpiece as described above, inner tube 14 is rotated within outer tube 12 by the handpiece motor. Openings 22, 24 at distal ends 26, 28 of tubes 12, 14, respectively, are periodically aligned as inner tube 14 rotates and admit tissue to be severed into instrument 10. Cutting implement 30 (e.g., sharpened edges of inner tube opening 22) cooperate with sharpened edges 32 of opening 24 in outer tube 12 to sever tissue caught between edges 30, 32 as inner tube rotates. Tissue thus cut is removed via a suction passage 34.

While a preferred embodiment has been described, other variations and modifications are within the scope of the following claims.

For example, interengaging segments 60 may have other dimensions. The length (L1) of segments 60 should be sufficiently small to enable segments 60 to move freely within outer tube 12 during operation (e.g., segments 60 should not be so long as to seize within outer tube 12 as inner tube 14 rotates). A flexible sheath, formed of, e.g., heat shrink tubing, may only surround the interengaging segments and the cutting implement. The tab and slot may not have rounded corners.

Surgical instrument 10 may be operable manually. Other materials may be used for, e.g., tubes 12, 14 and segments 60. The invention may be applied to instruments in fields other than arthroscopy.

What is claimed is:

1. A surgical instrument comprising
   an elongated outer member having an opening in a distal region thereof for admitting tissue, said outer member including a bend region that angularly offsets said distal region from a proximal region. of said outer member, an inner member, disposed within said outer member, having a cutting implement disposed in a distal region thereof, said inner member including a plurality of discrete, interengaging segments of limited length disposed within said bend region, at least one of said segments being configured to interengage a more proximal one and a more distal one of said segments to transmit force applied to a proximal region of said inner member through said bend region to said cutting implement to cause said cutting implement to move and cut tissue admitted through said opening, and a flexible sheath that surrounds said plurality of interengaging segments.

2. The surgical instrument of claim 1 wherein each segment has a length that is sufficiently small to enable said segment to freely move within said bend region.

3. The surgical instrument of claim 1 wherein each one of said interengaging segments includes at least one axially extending tab configured to be received by a portion of an adjacent one of said interengaging segments.

4. The surgical instrument of claim 1 wherein each one of said interengaging segments includes at least one slot configured to receive a portion of an adjacent one of said interengaging segments.

5. A surgical instrument comprising an elongated outer member having an opening in a distal region thereof for admitting tissue, said outer member including a bend region that angularly offsets said distal region from a proximal region of said outer member, an inner member, disposed within said outer member, having a cutting implement disposed in a distal region thereof, said inner member including a plurality of interengaging segments of limited length disposed within said bend region to transmit force applied to a proximal region of said inner member through said bend region to said cutting implement to cause said cutting implement to move and cut tissue admitted through said opening, each one of said interengaging segments including at least one tab that extends axially from an end of said one segment, and at least one slot disposed on an opposite end of said one segment, said at least one tab of one of said segments being received by said at least one slot of an adjacent one of said segments, and a flexible sheath that surrounds said plurality of interengaging segments.

6. A surgical instrument comprising an elongated outer member having an opening in a distal region thereof for admitting tissue, said outer member including a bend region that angularly offsets said distal region from a proximal region of said outer member, an inner member, disposed within said outer member, having a cutting implement disposed in a distal region thereof, said inner member including a plurality of interengaging segments of limited length disposed within said bend region to transmit force applied to a proximal region of said inner member through said bend region to said cutting implement to cause said cutting implement to move and cut tissue admitted through said opening, each one of said interengaging segments including at least one tab that extends axially from an end of said one segment, and at least one slot disposed in an opposite end of said one segment, said at least one tab of said one segment and said at least one slot of said one segment being offset by 90° from each other about a longitudinal axis of said segment, said at least one tab of one of said segments being received by said at least one slot of an adjacent one of said segments, and a flexible sheath that surrounds said plurality of interengaging segments.

7. A surgical instrument comprising an elongated outer member having an opening in a distal region thereof for admitting tissue, said outer member including a bend region that angularly offsets said distal region from a proximal region of said outer member, an inner member, disposed within said outer member, having a cutting implement disposed in a distal region thereof, said inner member including a plurality of interengaging segments of limited length disposed within said bend region to transmit force applied to a proximal region of said inner member through said bend region to said cutting implement to cause said cutting implement to move and cut tissue admitted through said opening, each one of said interengaging segments including at least one tab that extends axially from an end of said one segment, and at least one slot disposed in an opposite end of said one segment, said at least one tab having a length that exceeds a depth of said at least one slot, said at least one tab of one of said segments being received by said at least one slot of an adjacent one of said segments, and a flexible sheath that surrounds said plurality of interengaging segments.

8. The surgical instrument of claim 5 wherein said at least one tab has a width less than a width of said at least one slot.

9. The surgical instrument of claim 5 wherein said at least one tab has a rounded end surface.

10. The surgical instrument of claim 5 wherein said at least one tab and said at least one slot include rounded corners.

11. The surgical instrument of claim 1 wherein said inner member includes a rigid portion extending from a proximal region of the instrument to said bend region, said rigid portion configured to engage one of said interengaging segments.

12. The surgical instrument of claim 1 wherein said cutting implement is configured to engage one of said interengaging segments.

13. A surgical instrument comprising an elongated outer member having an opening in a distal region thereof for admitting tissue, said outer member including a bend region that angularly offsets said distal region from a proximal region of said outer member, an inner member, disposed within said outer member, having a cutting implement disposed in a distal region thereof, said inner member including a plurality of interengaging segments of limited length disposed within said bend region to transmit force applied to a proximal region of said inner member through said bend region to said cutting implement to cause said cutting implement to move and cut tissue admitted through said opening, and a flexible sheath that surrounds said plurality of interengaging segments and portions of said inner member and said cutting implement disposed adjacent to said plurality of interengaging segments.

14. The surgical instrument of claim 13 wherein said inner member and said plurality of interengaging segments are hollow to define a suction passage for transporting tissue cut by said cutting implement, said sheath sealing said suction passage.

15. A surgical instrument comprising an elongated outer member having an opening in a distal region thereof for admitting tissue, said outer member including a bend region that angularly offsets said distal region from a proximal region of said outer member, an inner member, disposed within said outer member, having a cutting implement disposed in a distal region thereof, said inner member including at least three discrete, interengaging segments of limited length disposed within said bend region to transmit force applied to a proximal region of said inner member through said bend region to said cutting implement to cause said cutting implement to move and cut tissue admitted through said opening, and a flexible sheath that surrounds said at least three interengaging segments.

* * * * *

UNITED STATES PATENT AND TRADEMARK OFFICE
CERTIFICATE OF CORRECTION

PATENT NO. : 5,755,731

DATED : May 26, 1998

INVENTOR(S) : Alexander Grinberg

It is certified that error appears in the above-identified patent and that said Letters Patent is hereby corrected as shown below:

Title page,

In the Foreign Patent Documents section, please delete the duplicated reference "9215255 9/1992 WIPO".

Col. 5, claim 1, line 2, replace "region." with --region--.

Signed and Sealed this

Eleventh Day of May, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,755,731
DATED : May 26, 1998
INVENTOR(S) : Alexander Grinberg

It is certified that error appears in the above-identified patent and that said Letters Patent is hereby corrected as shown below:

On the title page, replace
"[73] Assignee: Smith & Nephew Dyonics, Inc." with
--[73[ Assignee: Smith & Nephew, Inc.--

Signed and Sealed this

Sixth Day of July, 1999

Q. TODD DICKINSON

Attest:

Attesting Officer     Acting Commissioner of Patents and Trademarks